US011135162B2

United States Patent
Wahl et al.

(10) Patent No.: US 11,135,162 B2
(45) Date of Patent: Oct. 5, 2021

(54) PHARMACEUTICAL COMPOSITION IN THE FORM OF AN AQUEOUS SOLUTION, 1A SYRUP, CONTAINING INOSINE PRANOBEX AND ZINC GLUCONATE AND A METHOD OF PREPARATION THEREOF

(71) Applicant: AFLOFARM FARMACJA POLSKA SP. Z O.O., Pabianice (PL)

(72) Inventors: Hanna Wahl, Pabianice (PL); Marek Dąbrowa, Łódź (PL); Anna Ostrowska, Lutomiersk (PL); Małgorzata Kowalska - Parteka, Pabianice (PL); Jarosław Pasiński, Łódź (PL); Arkadiusz Madejczyk, Ksawerów (PL)

(73) Assignee: AFLOFARM FARMACJA POLSKA SP. Z O. O., Pabianice (PL)

( * ) Notice: Subject to any disclaimer, the term of this patent is extended or adjusted under 35 U.S.C. 154(b) by 0 days.

(21) Appl. No.: 16/631,026

(22) PCT Filed: Jun. 21, 2018

(86) PCT No.: PCT/PL2018/050029
§ 371 (c)(1),
(2) Date: Jan. 14, 2020

(87) PCT Pub. No.: WO2019/013658
PCT Pub. Date: Jan. 17, 2019

(65) Prior Publication Data
US 2020/0138709 A1 May 7, 2020

(30) Foreign Application Priority Data

Jul. 14, 2017 (PL) .......................... 422220

(51) Int. Cl.
| A61K 9/00 | (2006.01) |
| A61K 47/02 | (2006.01) |
| A61K 47/12 | (2006.01) |
| A61K 47/14 | (2017.01) |
| A61K 47/26 | (2006.01) |
| A61K 31/7076 | (2006.01) |
| A61K 33/30 | (2006.01) |
| A61K 47/10 | (2017.01) |

(52) U.S. Cl.
CPC ........ *A61K 9/0095* (2013.01); *A61K 31/7076* (2013.01); *A61K 33/30* (2013.01); *A61K 47/02* (2013.01); *A61K 47/10* (2013.01); *A61K 47/12* (2013.01); *A61K 47/14* (2013.01); *A61K 47/26* (2013.01)

(58) Field of Classification Search
CPC .......... A61K 9/00; A61K 47/02; A61K 47/12; A61K 47/14; A61K 47/26; A61K 31/7076; A61K 33/30
See application file for complete search history.

(56) References Cited

U.S. PATENT DOCUMENTS

| 2009/0016990 A1* | 1/2009 | Alberte | ................ A61K 31/185 |
| | | | 424/85.5 |
| 2009/0221563 A1* | 9/2009 | Biesmans | .......... A61K 31/5415 |
| | | | 514/226.5 |
| 2012/0082720 A1* | 4/2012 | Ang | ........................ A61P 31/22 |
| | | | 424/463 |
| 2012/0321571 A1* | 12/2012 | Edelson | ............. A61K 31/4439 |
| | | | 424/59 |
| 2018/0303874 A1* | 10/2018 | Mullin | .................... A61P 31/12 |

FOREIGN PATENT DOCUMENTS

| JP | 2006131618 A | 5/2006 |
| UA | 32464 U | 5/2008 |
| WO | 2006138518 A1 | 12/2006 |
| WO | 2012096655 A1 | 7/2012 |

OTHER PUBLICATIONS

International Search Report, PCT/PL2018/050029, dated Sep. 24, 2018.
Written Opinion of the International Searching Authority, PCT/PL2018/050029, dated Sep. 24, 2018.

* cited by examiner

*Primary Examiner* — Zohreh A Fay
(74) *Attorney, Agent, or Firm* — Arrigo, Lee, Guttman & Mouta-Bellum LLP

(57) ABSTRACT

The invention relates to a pharmaceutical composition in the form of an aqueous solution, preferably a syrup, containing inosine pranobex and zinc gluconate, characterised in that it contains a sweetener selected from the group of disaccharides, preferably sucrose or/and from the group of polyols, preferably maltitol, a solubilizer from the group of hydroxy alcohols or mixtures thereof, preferably propylene glycol, glycerol, preservatives selected from the group of parahydroxybenzoic acid esters and mixtures thereof, preferably methyl parahydroxybenzoate, propyl parahydroxybenzoate, a sweetener, preferably sodium saccharine or sucralose, and pH regulators in the range from 5.7 to 12.0 preferably aroma, and a method of preparation thereof.

15 Claims, No Drawings

PHARMACEUTICAL COMPOSITION IN THE FORM OF AN AQUEOUS SOLUTION, 1A SYRUP, CONTAINING INOSINE PRANOBEX AND ZINC GLUCONATE AND A METHOD OF PREPARATION THEREOF

The invention relates to a pharmaceutical composition in the form of an aqueous solution, preferably a syrup, containing inosine pranobex and zinc gluconate and a method of preparation thereof. The invention can be used in pharmacy.

A drug is known in the art by the name of Eloprine in the form of a syrup, produced by the company Polfarmex SA, whose composition comprises, in addition to inosine pranobex, also methyl parahydroxybenzoate, propyl parahydroxybenzoate, sucrose, monohydrate citric acid, sodium hydroxide, aroma and water. A drug is known by the name of Groprinosin from the company Gedeon Richter Polska Sp. z o.o., containing the same active ingredient and adjuvants such as sucrose, sodium saccharin, methyl parahydroxybenzoate, propyl parahydroxybenzoate, purified water, glycerol, 96% ethanol and aroma. A drug is known to contain said active ingredient by the name of Isoprinosine from the company Ewopharma International s.r.o. containing sucrose, methyl parahydroxybenzoate, propyl parahydroxybenzoate, sodium hydroxide, aroma, sodium citrate and purified water. Another drug of the same form containing the same active ingredient is Neosine from the company Aflofarm Farmacja Polska Sp. z o.o., which contains additional adjuvants such as methyl parahydroxybenzoate, propyl parahydroxybenzoate, sucrose, citric acid, sodium hydroxide, propylene glycol, aroma and purified water. A drug Pranosin from the company Galena is known to contain said active ingredient and, in addition, sucrose, methyl parahydroxybenzoate, propyl parahydroxybenzoate, sodium citrate, sodium hydroxide (pH needs to be determined), raspberry flavour, purified water. The international application WO2012096655A1 discloses a medicinal composition containing alkylglycerols, artemidin, common mushroom, chlorophyllin and inosine and zinc. Preliminary preformulation studies show that the combination of inosine pranobex and zinc gluconate in an aqueous solution triggers a chemical reaction yielding a precipitate inadmissible according to the assumptions made regarding the new formulation of the medicinal product and the unpleasant taste of the solution. During studies on the medicinal product with inosine pranobex and zinc gluconate in the form of an aqueous solution, the composition of the commercial medicinal product containing 500 mg/5 ml of inosine pranobex was reconstituted, and zinc gluconate was added. Likewise, a precipitate was observed that prevented the use of such formulation as the target pharmaceutical composition of the medicinal product. There is still a need to provide a pharmaceutical composition and a method of preparation thereof with inosine pranobex and zinc gluconate, which mediates proper functioning of the immune system, with its liquid form in the form of an aqueous solution, preferably a syrup, being free from precipitate and unpleasant taste. Surprisingly, the above problem has been solved by means of the invention disclosed.

The first object of the invention is a pharmaceutical composition in the form of an aqueous solution, preferably a syrup, containing inosine pranobex and zinc gluconate, characterised in that it contains a sweetener selected from the group of disaccharides, preferably sucrose or/and from the group of polyols, preferably maltitol, a solubilizer from the group of hydroxy alcohols or mixtures thereof, preferably propylene glycol, glycerol, preservatives selected from the group of parahydroxybenzoic acid esters and mixtures thereof, preferably methyl parahydroxybenzoate, propyl parahydroxybenzoate, a sweetener, preferably sodium saccharine or sucralose, and pH regulators in the range from 5,7 to 12,0, preferably aroma. It is also preferred for the composition of to the invention to be characterised in that the pH regulators are selected from the group comprising sodium hydroxide and citric acid. It is also preferred for the composition of to the invention to be characterised in that it contains from 0.05% to 13% inosine pranobex and from 0.349% to 2.106% zinc gluconate. In a further preferred embodiment of the invention, the composition contains inosine pranobex and zinc gluconate in an amount of 500 mg/5 ml and 3.125 mg zinc ions/5 ml, respectively. It is also preferred for the composition of to the invention to be characterised in that it contains methyl parahydroxybenzoate (m-paraben) in the range of 0.08÷0.18% and propyl parahydroxybenzoate (p-paraben) in the range of 0.01÷0.02%.

A second object of the invention is a method of preparation of the composition disclosed in the first object of the invention characterised in that it comprises:

a) dissolving the sweetener in water;

b) cooling the solution from step a)

c) adding to the solution from step b) a solubilizer from the group of hydroxy alcohols or mixtures thereof;

d) adding to the solution of step c) preservatives selected from the group of parahydroxybenzoic acid esters and mixtures thereof until dissolution e) cooling the solution from step d)

f) adding the sweetener to the solution of step e)

g) adding pH regulators;

h) sequentially adding, until dissolution, inosine pranobex and then zinc gluconate, followed by cooling, and preferably adding the aroma.

The invention disclosed makes it possible to obtain a liquid form of the drug, which is characterised by stability despite the use of two active ingredients, and a better taste than medicinal products containing only inosine pranobex.

Example No. 1 Method Of Preparation

The invention relates to a liquid medicinal product containing a combination of two active ingredients of inosine pranobex and zinc gluconate in an amount of 500 mg/5 ml and 3.125 mg zinc ions/5 ml respectively, a sweetener from the group of disaccharides, e.g. sucrose or from the group of polyols, e.g. maltitol, a solubilizer from the group of hydroxy alcohols or mixtures thereof, e.g. propylene glycol, glycerol, preservatives from the group of parahydroxybenzoic acid esters and mixtures thereof, e.g. methyl parahydroxybenzoate (m-paraben in the range of 0.08÷0.18%), propyl parahydroxybenzoate (p-paraben) in the range of 0.01÷0.02%), and a sweetener, e.g. sodium saccharin, sucralose, free of precipitate and characterised by a better taste than a product containing only one active ingredient: inosine pranobex. For the above combination in liquid form, a product was developed with two main pharmaceutical compositions similar to each other. The pharmaceutical compositions of the medicinal product, syrup/oral solution are shown in Table 1:

TABLE 1

Pharmaceutical compositions of the medicinal product containing a combination of two active ingredients of inosine pranobex and zinc gluconate in liquid form

| Item | Starting material | Oral solution Amount [g/100 g] | Sirup Amount [g/100 g] |
|---|---|---|---|
| 1 | Inosine pranobex | 8.21 | 8.04 |
| 2 | Zinc gluconate | 0.356 | 0.349 |
| 3 | Propylene glycol | 8.0 | 4.0 |
| 4 | Sucrose | 40.0 | 45.0 |
| 5 | Methyl parahydroxybenzoate | 0.16 | 0.16 |
| 6 | Propyl parahydroxybenzoate | 0.018 | 0.018 |
| 7 | Citric acid | qs. | qs. |
| 8 | Sodium hydroxide | qs. | qs. |
| 9 | Sodium saccharin | 0.1 | 0.1 |
| 10 | Aroma | 0.05 | 0.05 |
| 11 | Purified water | ad 100 g | ad 100 g |

The method of preparation for both pharmaceutical compositions is analogous and it is as follows:

Add sucrose into purified water and bring it to boil. Maintain the temperature for 2÷4 minutes. Then cool the solution. Add propylene glycol, stir. Add methyl parahydroxybenzoate and propyl parahydroxybenzoate to the solution and stir until the substance dissolves. Cool the solution. Add sodium saccharin and stir until the substance dissolves. Add citric acid and mix until the substance dissolves. Add sodium hydroxide, stir. Add the determined amount of inosine pranobex and stir until the substance dissolves. Add the determined amount of zinc gluconate and stir until the substance dissolves. Cool the solution. Add aroma, stir.

The invention disclosed makes it possible to obtain a liquid form of the drug, which is characterised by stability despite the use of two active ingredients in liquid form, and a better taste than medicinal products containing only inosine pranobex.

Example No. 2 Development of a Liquid Form Drug Formulation for the Combination of Active Ingredients of Inosine Pranobex and Zinc Gluconate—Preliminary Studies At the preliminary stage of research on the medicinal product with inosine pranobex and zinc gluconate in liquid form, the composition of the commercial medicinal product containing inosine pranobex in a concentration of 500 mg/5 ml was reconstituted and zinc gluconate was added. A precipitate was observed.

Example 2a. Selection of Buffer Substance/pH Regulator

The next stage of the research was to verify whether the precipitate forms appear in the aqueous solution of inosine pranobex and zinc gluconate in the presence of other buffering substances. (str 6) For this purpose, technological samples were prepared with the compositions shown in Table 2. The buffer system was selected so that the pH of the aqueous solution was approx. 6.0.

TABLE 2

Technological samples of an aqueous solution of inosine pranobex and zinc gluconate with different buffer substances.

Test objective: Determines the form of aqueous solution of two APIs with different buffers

| Starting material | Pa 1 | Pa 2 | Pa 3 | Pa 4 | Pa 5 | Pa 6 | Pa 7 | Pa 8 | Pa 9 | Pa 10 | Pa 11 | Pa 12 | Pa 13 |
|---|---|---|---|---|---|---|---|---|---|---|---|---|---|
| Inosine pranobex | 8.13 | 8.13 | 8.13 | 8.13 | 8.13 | 8.13 | 8.13 | 8.13 | 8.13 | 8.13 | 8.13 | 8.13 | 8.13 |
| Zinc gluconate | 0.353 | 0.353 | 0.353 | 0.353 | 0.353 | 0.353 | 0.353 | 0.353 | 0.353 | 0.353 | 0.353 | 0.353 | 0.353 |
| Sodium dihydrogen phosphate | 0.37 | 0.35 | 0.34 | | | 0.34 | | | | | | | |
| Sodium hydrogen phosphate | 0.31 | 0.30 | | 0.28 | | | 0.28 | | | 0.29 | | | |
| Diluted phosphoric acid | | 0.08 | | 0.3 | 0.08 | | | 0.08 | | | | | |
| Sodium hydroxide | | | 0.12 | | 0.04 | | | | 0.06 | | | | 0.22 |
| Citric acid | | | | | | | 0.032 | | | | | | 0.40 |
| Sodium citrate | | | | | | 0.22 | | 0.24 | | | 0.15 | 0.15 | |
| Hydrochloric acid 10% | | | | | | | | | 0.06 | 0.16 | 0.02 | | |
| Purified water | 40.0 | 40.0 | 40.0 | 40.0 | 40.0 | 40.0 | 40.0 | 40.0 | 40.0 | 40.0 | 40.0 | 40.0 | 40.0 |
| pH of the solution after adding excipients | 6.3 | 6.0 | 6.0 | 6.2 | 6.5 | 5.9 | 6.5 | 6.2 | 6.1 | 5.9 | 6.3 | 6.0 | 6.2 |
| pH of the final solution with API | 6.0 | 6.0 | 5.8 | 5.9 | 6.4 | 6.0 | 6.1 | 6.3 | 6.7 | 5.9 | 6.5 | 6.3 | 6.0 |
| Form: | clear transparent solution | | | | | Turbid solution | | | | | | | Clear solution |

Surprisingly, it turned out that the aqueous solution of the combined active ingredients of inosine pranobex and zinc gluconate is clear only in the combination of citric acid and sodium hydroxide (sample 13). Solutions prepared by combining the test active ingredients with other buffer substances did not yield a clear solution.

Example 2b. Determination of the Proportion of pH Regulators and the pH Range

Further research involved the determination of the pH range of the aqueous solution of the combination of two active ingredients of inosine pranobex and zinc gluconate using different amounts of citric acid and sodium hydroxide. The process of preparation of technological samples consisted in the dissolution of citric acid and sodium hydroxide in purified water, after which inosine pranobex was added to the resulting solution and stirred until dissolution, then zinc gluconate was added and stirred mixed until dissolution. Tables 3÷5 show the compositions of technological samples together with observations.

TABLE 3

Technological samples of an aqueous solution of inosine pranobex and zinc gluconate with different contents of citric acid and a constant content of sodium hydroxide.

Test objective: Determination of the form of aqueous solution of two APIs with different amounts of citric acid and a constant content of sodium hydroxide

| Starting material | Pa 14 | Pa 15 | Pa 16 | Pa 17 | Pa 18 |
|---|---|---|---|---|---|
| Inosine pranobex | 8.13 | 8.13 | 8.13 | 8.13 | 8.13 |
| Zinc gluconate | 0.353 | 0.353 | 0.353 | 0.353 | 0.353 |
| Sodium hydroxide | 0.22 | 0.22 | 0.22 | 0.22 | 0.22 |
| Citric acid | 0.01 | 0.35 | 0.45 | 0.50 | 1.0 |
| Purified water | 40.0 | 40.0 | 40.0 | 40.0 | 40.0 |
| Form | Turbid solution | Clear solution | Precipitate | Precipitate | Precipitate |
| pH | 8.6 | 8.3 | — | — | 5.7 |

TABLE 4

Technological samples of an aqueous solution of inosine pranobex and zinc gluconate with different contents of sodium hydroxide and a constant content of citric acid.

Objective of the test: Determination of the form of aqueous solution of two APIs with different amounts of sodium hydroxide and a constant content of citric acid

| Starting material | Pa 19 | Pa 20 | Pa 21 | Pa 22 | Pa 23 |
|---|---|---|---|---|---|
| Inosine pranobex | 8.13 | 8.13 | 8.13 | 8.13 | 8.13 |
| Zinc gluconate | 0.353 | 0.353 | 0.353 | 0.353 | 0.353 |
| Sodium hydroxide | 0.01 | 0.20 | 0.21 | 0.45 | 1.0 |
| Citric acid | 0.40 | 0.40 | 0.40 | 0.40 | 0.40 |
| Purified water | 40.0 | 40.0 | 40.0 | 40.0 | 40.0 |
| Form | Precipitate is formed | Precipitate is formed | Clear solution | Clear solution | Precipitate has not dissolved |
| pH | 5.7 | 5.8 | 5.9 | 8.6 | |

TABLE 5

Technological samples of an aqueous solution of inosine pranobex and zinc gluconate with different contents of sodium hydroxide and of citric acid.

Objective of the test: Determination of the form of aqueous solution of two APIs with different amounts of sodium hydroxide and of citric acid

| Starting material | Pa 24 | Pa 25 | Pa 26 | Pa 27 | Pa 28 |
|---|---|---|---|---|---|
| Inosine pranobex | 8.13 | 8.13 | 8.13 | 8.13 | 8.13 |
| Zinc gluconate | 1.353 | 0.353 | 0.353 | 0.353 | 0.353 |
| Sodium hydroxid | 0.21 | 0.55 | 0.60 | 0.70 | 0.0695 |
| Citric acid | 0.35 | 0.40 | 0.40 | 0.40 | 0.126 |
| Purified water | 40.0 | 40.0 | 40.0 | 40.0 | 40.0 |
| Form | Clear solution | Clear solution | Precipitate is formed | Precipitate | Clear solution |
| pH | 6.9 | 8.9 | 9.0 | 9.5 | 7.0 |

In the technological samples conducted of an aqueous solution of the combination of two active ingredients of inosine pranobex and zinc gluconate with a different content of citric acid and sodium hydroxide, turbidity of said solution or precipitation was observed. Surprisingly, it turned out that the use of citric acid in the range of 0.126 g/100 g-0.40 g/100 g and sodium hydroxide in the range of 0.695/100 g-0.55 g/100 g yields a fluid form of the drug free from precipitate and turbidity.

Example 3. Determination of the Composition and Technology of Preparation of the Medicinal Product Since the use of a proportion of the other ingredients forming a liquid form of the drug such as in the monoformulation containing inosine pranobex proved ineffective, as, surprisingly, it was found that the addition of a small amount of zinc gluconate reduced solubility of both active ingredients in the liquid form of the drug, a composition of excipients was used experimentally, especially the proportion of propylene glycol and sucrose, which in the proportions listed below (Table 6) surprisingly yielded physical stability of the liquid form of the drug containing a combination of inosine pranobex and zinc gluconate.

TABLE 6

Technological samples of the medicinal product containing a combination of two active ingredients of inosine pranobex and zinc gluconate in liquid form involving precipitate elimination.

| | Objective of the test: Selection of excipients propylene glycol and sucrose for precipitate elimination. | |
|---|---|---|
| Starting material | Pa 29 | Pa 30 |
| Inosine pranobex | 8.21 | 8.04 |
| Zina gluconate | 0.353 | 0.353 |
| Propylene glycol | 4.0 | 8.0 |
| Sucrose | 45.0 | 40.0 |

TABLE 6-continued

Technological samples of the medicinal product containing a combination of two active ingredients of inosine pranobex and zinc gluconate in liquid form involving precipitate elimination.

| | Objective of the test: Selection of excipients propylene glycol and sucrose for precipitate elimination. | |
|---|---|---|
| Starting material | Pa 29 | Pa 30 |
| Methyl parahydroxybenzoate | 0.18 | 0.18 |
| Propyl parahydroxybenzoate | 0.02 | 0.02 |
| Citric acid | 0.40 | 0.40 |
| Sodium hydroxide | 0.22 | 0.22 |
| Sodium saccharin | 0.1 | 0.1 |
| Banana flavour | 0.05 | 0.05 |
| Purified water | ad 100 | ad 100 |
| Form | Transparent solution - no changes in the form after 2.5 months of storing refrigerated | Transparent solution - no changes in the form after 2.5 months of storing refrigerated |
| pH | 6.1 | 6.1 |

Compositions of samples 29 and 30 yielded a positive result of precipitate elimination in the medicinal product containing a combination of two active ingredients of inosine pranobex and zinc gluconate in liquid form. Surprisingly, it was also found that the taste of the resulting product compared to the monoformulation containing only inosine pranobex is improved.

Example 3.1 Determination of the Limit Concentrations of pH Regulators and the pH of the Final Product The above observations from the tests to determine the proportion of pH regulators and the pH range were repeated on the finished medicinal product in a liquid form containing a combination of two active ingredients of inosine pranobex and zinc gluconate. For this purpose, a medicinal product with different pH was prepared and the form of the product was observed. Tables 7 (a and b) and 8 (a and b) show the composition and observations

TABLE 7a

A medicinal product containing a combination of two active ingredients of inosine pranobex and zinc gluconate in a liquid form with a lower sucrose content with different pH and a constant content of citric acid

| | Objective of the test: Determination of the effect of pH on the product with a lower amount of sucrose | | | | |
|---|---|---|---|---|---|
| Starting material | Pa 31 | Pa 32 | Pa 33 | Pa 34 | Pa 35 |
| Inosine pranobex | 8.13 | 8.13 | 8.13 | 8.13 | 8.13 |
| Zinc gluconate | 0.353 | 0.353 | 0.353 | 0.353 | 0.353 |
| Propylene glycol | 8.0 | 8.0 | 8.0 | 8.0 | 8.0 |
| Sucrose | 40.0 | 40.0 | 40.0 | 40.0 | 40.0 |
| Methyl parahydroxybenzoate | 0.18 | 0.18 | 0.16 | 0.16 | 0.16 |
| Propyl parahydroxybenzoate | 0.02 | 0.02 | 0.018 | 0.018 | 0.018 |
| Citric acid | q.s (0.48) | 0.40 | 0.40 | 0.40 | 0.40 |
| Sodium hydroxide | 0.2 | 0.22 | q.s (2.62) | q.s (3.71) | q.s (5.24) |
| Sodium saccharin | 0.1 | 0.1 | 0.1 | 0.1 | 0.1 |
| Banana flavour AR0010 | 0.05 | 0.05 | 0.05 | 0.05 | 0.05 |
| Purified water | ad 100 | ad 100 | ad 100 | ad 100 | ad 100 |
| Form | Clear solution | compliant | compliant | compliant | Precipitate is formed |
| pH | 5.5 | 6.0 | 11.5 | <12 | >12 |

TABLE 7b

A medicinal product containing a combination of two active ingredients of inosine pranobex and zinc gluconate in a liquid form with a lower sucrose content with different pH and a constant content of sodium hydroxide

| | Objective of the test: Determination of the effect of pH on the product with a lower amount of sucrose | | |
|---|---|---|---|
| Starting material | Pa 36 | Pa 37 | Pa 38 |
| Inosine pranobex | 8.13 | 8.13 | 8.13 |
| Zinc gluconate | 0.353 | 0.353 | 0.353 |
| Propylene glycol | 8.0 | 8.0 | 8.0 |
| Sucrose | 40.0 | 40.0 | 40.0 |
| Methyl parahydroxybenzoate | 0.18 | 0.18 | 0.16 |
| Propyl parahydroxybenzoate | 0.02 | 0.02 | 0.018 |
| Citric acid | 0.10 | 0.35 | 0.45 |
| Sodium hydroxide | 0.22 | 0.22 | 0.22 |
| Sodium saccharin | 0.1 | 0.1 | 0.1 |
| Banana flavour | 0.05 | 0.05 | 0.05 |
| Purified water | ad 100 | ad 100 | ad 100 |
| Form | precipitate | compliant | precipitate |
| pH | 12.0 | 8.4 | 5.6 |

TABLE 8a

A medicinal product containing a combination of two active ingredients of inosine pranobex and zinc gluconate in a liquid form with a lower content of propylene glycol with different pH and a constant content of citric acid Objective of the test: Determination of the effect of pH on the product with a lower amount of propylene glycol

| Starting material | Pa 39 | Pa 40 | Pa 41 | Pa 42 |
|---|---|---|---|---|
| Inosine pranobex | 8.13 | 8.13 | 8.13 | 8.13 |
| Zinc gluconate | 0.353 | 0.353 | 0.353 | 0.353 |
| Propylene glycol | 4.0 | 4.0 | 4.0 | 4.0 |
| Sucrose | 45.0 | 45.0 | 45.0 | 45.0 |
| Methyl parahydroxybenzoate | 0.18 | 0.18 | 0.16 | 0.16 |
| Propyl parahydroxybenzoate | 0.02 | 0.02 | 0.018 | 0.018 |
| Citric acid | q.s. (0.48) | 0.40 | 0.40 | 0.40 |
| Sodium hydroxide | 0.22 | 0.22 | q.s (1.96) | q.s (3.93) |
| Sodium saccharin | 0.1 | 0.1 | 0.1 | 0.1 |
| Banana flavour | 0.05 | 0.05 | 0.05 | 0.05 |
| Purified water | ad 100 | ad 100 | ad 100 | ad 100 |
| Form | Clear solution | compliant | compliant | turbidity |
| pH | 5.7 | 5.9 | 10.8 | 11.9 |

TABLE 8b

A medicinal product containing a combination of two active substances of inosine pranobex and zinc gluconate in a liquid form with a lower content of propylene glycol with different pH and a constant content of sodium hydroxide Objective of the test: Determination of the effect of pH on the product with a lower amount of propylene glycol

| Starting material | Pa 43 | Pa 44 | Pa 45 |
|---|---|---|---|
| Inosine pranobex | 8.13 | 8.13 | 8.13 |
| Zinc gluconate | 0.353 | 0.353 | 0.353 |
| Propylene glycol | 4.0 | 4.0 | 4.0 |
| Sucrose | 45.0 | 45.0 | 45.0 |
| Methyl parahydroxybenzoate | 0.18 | 0.18 | 0.16 |
| Propyl parahydroxybenzoate | 0.02 | 0.02 | 0.018 |
| Citric acid | 0.10 | 0.35 | 0.45 |
| Sodium hydroxide | 0.22 | 0.22 | 0.22 |
| Sodium saccharin | 0.1 | 0.1 | 0.1 |
| Banana flavour | 0.05 | 0.05 | 0.05 |
| Purified water | ad 100 | ad 100 | ad 100 |
| Form | Clear solution | compliant | compliant |
| pH | 12.0 | 6.1 | 5.7 |

The presented results of observations of the medicinal product form in liquid form containing a combination of two active ingredients of inosine pranobex and zinc gluconate, it was observed that the product forms a precipitate below pH 5.7 and above 12.0. Surprisingly, it was found that only in the pH range above 5.7 and below 12.0 the product is stable, clear and free of precipitate and/or, for sodium hydroxide concentration in the range of 0.22 g/100 g-3.71 g/100 g, equally preferably citric acid 0.35 g/100 g-0.45 g/100 g Example 3.2 Determination of the Correct Order of Adding Ingredients Since in the course of research on the selection of proper proportions of ingredients forming formulations of the liquid form of the drug containing a combination of two active ingredients of inosine pranobex and zinc gluconate, it was observed that the order of adding ingredients affects the stability of the medicinal product, at the subsequent stage of research a series of technological samples were performed in order to identify the effect of the order of adding substances, especially buffer and active ingredients, on precipitate formation. For this purpose, technological samples were performed of the aqueous solution of inosine pranobex and zinc gluconate with pH regulators, in which active ingredients and excipients were added to the solution in different orders. Table 9 shows the compositions and the method of preparation.

TABLE 9

Technological samples with different method of adding active ingredients and excipients Objective of the test: Invention - testing the order of adding substances.

| Starting material | Pa 46 | Pa 47 | Pa 48 |
|---|---|---|---|
| Inosine pranobex | 8.13 | 8.13 | 8.13 |
| Zinc gluconate | 0.353 | 0.353 | 0.353 |
| Citric acid | 0.22 | 0.22 | 0.22 |
| Sodium hydroxide | 0.40 | 0.40 | 0.40 |
| Purified water | 40.0 | 40.0 | 40.0 |
| Preparation method | Add citric acid to purified water, stir. Add sodium hydroxide solution, stir. Add inosine pranobex, stir. Add zinc gluconate, stir. | Add inosine pranobex to purified water, stir. Add zinc gluconate, stir. Add citric acid, stir. Add sodium hydroxide, stir. | Add inosine pranobex to purified water, stir. Add zinc gluconate, stir. Add the prepared aqueous solution of citric acid and sodium hydroxide, stir. |

TABLE 9-continued

Technological samples with different method of adding active ingredients and excipients Objective of the test:
Invention - testing the order of adding substances.

| Starting material | Pa 46 | Pa 47 | Pa 48 |
|---|---|---|---|
| Form | Clear solution | Slight precipitate is formed | Clear solution |
| pH | 6.0 | 5.9 | 6.2 |

Surprisingly, it was found that despite maintaining the appropriated predetermined pH of the product and the proportion of ingredients added, the only correct order of adding active and buffer substances is presented in the sample 46. Surprisingly, it was found that buffer substances must be added and dissolved in the solution before the addition of the active ingredients.

Example 3.3 Determination of the Limit Concentrations of the Active Ingredients Used The next stage of research was to check the form of the medicinal product in a liquid form containing a combination of two active ingredients inosine pranobex and zinc gluconate using the minimum and maximum therapeutic doses of active ingredients. For this purpose, technological samples were performed with the lowest amount of inosine pranobex and/or zinc gluconate and with the highest amount of inosine pranobex and/or zinc gluconate, and the product form was observed. Tables 10 and 11 show the compositions of technological samples and observations.

TABLE 10

The product tested in a liquid form (with a lower amount of propylene glycol) with different therapeutic doses of active ingredients Objective of the test:
Determinatean of the APT therapeutic range in the product without precipitate - with a lower amount of propylene glycol

| Starting material | Pa 49 | Pa 50 | Pa 51 | Pa 52 | Pa 53 | Pa 54 | Pa 55 | Pa 56 |
|---|---|---|---|---|---|---|---|---|
| Inosine pranobex | 0.05 | 8.13 | 0.05 | 13.0 | 13.5 | 8.04 | 8.04 | 13.0 |
| Zinc gluconate | 0.349 | 0.0017 | 0.0017 | 0.349 | 0.349 | 1.606 | 1.706 | 1.606 |
| Propylene glycol | 4.0 | 4.0 | 4.0 | 4.0 | 4.0 | 4.0 | 4.0 | 4.0 |
| Surcose | 45.0 | 45.0 | 45.0 | 45.0 | 45.0 | 45.0 | 45.0 | 45.0 |
| Methyl parahydroxybenzoate | 0.16 | 0.16 | 0.16 | 0.16 | 0.16 | 0.16 | 0.16 | 0.16 |
| Propyl parahydroxybenzoate | 0.018 | 0.018 | 0.018 | 0.018 | 0.018 | 0.018 | 0.018 | 0.018 |
| Citric acid | 0.40 | 0.40 | 0.40 | 0.40 | 0.40 | 0.40 | 0.40 | 0.40 |
| Sodium hydroxide | 0.22 | 0.22 | 0.22 | 0.22 | 0.22 | 0.22 | 0.22 | 0.22 |
| Sodium saccharin | 0.1 | 0.1 | 0.1 | 0.1 | 0.1 | 0.1 | 0.1 | 0.1 |
| Banana flavor | 0.05 | 0.05 | 0.05 | 0.05 | 0.05 | 0.05 | 0.05 | 0.05 |
| Purified water | ad 100 | ad 100 | ad 100 | ad 100 | ad 100 | ad 100 | ad 100 | ad 100 |
| From: | compliant | compliant | compliant | compliant | Turbid solution | compliant | Precipitate has formed | Precipitate has formed |

TABLE 11

The product tested in a liquid form (with a lower amount of sucrose) with different therapeutic doses of active ingredients Objective of the test:
Determination of the API therapeutic range in the product without precipitate

| Starting Material | Pa 57 | Pa 58 | Pa 59 | Pa 60 | Pa 61 | Pa 62 | Pa 63 | Pa 64 |
|---|---|---|---|---|---|---|---|---|
| Inosine pranobex | 0.05 | 8.21 | 0.05 | 13.0 | 13.5 | 8.21 | 8.21 | 13.0 |
| Zinc gluconate | 0.356 | 0.0017 | 0.0017 | 0.356 | 0.356 | 2.106 | 2.156 | 2.106 |
| Propylene glycol | 8.0 | 8.0 | 8.0 | 8.0 | 8.0 | 8.0 | 8.0 | 8.0 |

TABLE 11-continued

The product tested in a liquid form (with a lower amount of sucrose) with different therapeutic doses of active ingredients Objective of the test:
Determination of the API therapeutic range in the product without precipitate

| Starting Material | Pa 57 | Pa 58 | Pa 59 | Pa 60 | Pa 61 | Pa 62 | Pa 63 | Pa 64 |
|---|---|---|---|---|---|---|---|---|
| Surcose | 40.0 | 40.0 | 40.0 | 40.0 | 40.0 | 40.0 | 40.0 | 40.0 |
| Methyl parahydroxybenzoate | 0.16 | 0.16 | 0.16 | 0.16 | 0.16 | 0.16 | 0.16 | 0.16 |
| Propyl parahydroxybenzoate | 0.018 | 0.018 | 0.018 | 0.018 | 0.018 | 0.018 | 0.018 | 0.018 |
| Citric acid | 0.40 | 0.40 | 0.40 | 0.40 | 0.40 | 0.40 | 0.40 | 0.40 |
| Sodium hydroxide | 0.22 | 0.22 | 0.22 | 0.22 | 0.22 | 0.22 | 0.22 | 0.22 |
| Sodium saccharin | 0.1 | 0.1 | 0.1 | 0.1 | 0.1 | 0.1 | 0.1 | 0.1 |
| Banana flavor | 0.05 | 0.05 | 0.05 | 0.05 | 0.05 | 0.05 | 0.05 | 0.05 |
| Purified water | ad 100 | ad 100 | ad 100 | ad 100 | ad 100 | ad 100 | ad 100 | ad 100 |
| Form | compliant | compliant | compliant | compliant | Precipitate has formed | compliant | Precipitate has formed | Precipitate has formed |

The technological samples performed demonstrated that the product with the lowest amounts of active ingredients of inosine pranobex and/or zinc gluconate in the product in liquid form is clear without precipitate. However, for a product with a lower amount of propylene glycol, it was surprisingly found that the use of more than 13.0% content of inosine pranobex and/or 1.606% of zinc gluconate, and in a medicinal product with a lower amount of sucrose and the use of more than 13.0% content of inosine pranobex and/or 2.106% content of zinc gluconate causes precipitate to form.

The invention claimed is:

1. An aqueous pharmaceutical composition, comprising:
   from 0.05% to 13% inosine pranobex,
   from 0.349% to 2.106% zinc gluconate,
   from 0.22% to 3.71% sodium hydroxide, and
   from 0.35% to 0.45% citric acid;
   wherein the pH of the aqueous pharmaceutical composition is above 5.7 and below 12.0; and
   wherein the aqueous pharmaceutical composition is clear and free of precipitate.

2. The aqueous pharmaceutical composition according to claim 1, in the form of a solution.

3. The aqueous pharmaceutical composition according to claim 1, in the form of a syrup.

4. The aqueous pharmaceutical composition according to claim 1, further comprising a disaccharide sweetener or a polyol sweetener.

5. The aqueous pharmaceutical composition according to claim 4, wherein the disaccharide sweetener is sucrose.

6. The aqueous pharmaceutical composition according to claim 4, wherein the polyol sweetener is maltitol.

7. The aqueous pharmaceutical composition according to claim 1, further comprising a hydroxy alcohol that increases solubility.

8. The aqueous pharmaceutical composition according to claim 7, wherein the hydroxy alcohol is propylene glycol or glycerol.

9. The aqueous pharmaceutical composition according to claim 1, further comprising a parahydroxybenzoic acid ester preservative.

10. The aqueous pharmaceutical composition according to claim 9, wherein the parahydroxybenzoic acid ester preservative is methyl parahydroxybenzoate, propyl parahydroxybenzoate, or a mixture thereof.

11. The aqueous pharmaceutical composition according to claim 1, further comprising saccharine or sucralose.

12. The aqueous pharmaceutical composition according to claim 1, wherein the concentration of inosine pranobex in the composition is 500 mg/5 ml and the concentration of zinc ions is 3.125 mg/5 ml.

13. The aqueous pharmaceutical composition according to claim 1, further comprising from 0.08% to 0.18% methyl parahydroxybenzoate paraben and from 0.01% to 0.02% propyl parahydroxybenzoate (p-paraben).

14. A method making the pharmaceutical composition according to claim 1, comprising:
   a) dissolving a disaccharide sweetener or a polyol sweetener in water;
   b) cooling the solution from step a),
   c) adding to the solution from step b) a hydroxy alcohol to increase solubility,
   d) adding to the solution of step c) a parahydroxybenzoic acid ester preservative until dissolution,
   e) cooling the solution from step d)
   f) adding saccharine or sucralose to the solution of step e),
   g) adding the sodium hydroxide and the citric acid to provide a pH of the aqueous pharmaceutical composition of above 5.7 and below 12.0,
   h) adding inosine pranobex to the solution of step g) until dissolution,
   i) adding zinc gluconate to the solution of step h) until dissolution, and
   j) cooling the solution of step i).

15. The method making according to claim 14, further comprising adding an aroma.

* * * * *